US00PP11852P2

(12) United States Plant Patent
Glicenstein

(10) Patent No.: US PP11,852 P2
(45) Date of Patent: May 1, 2001

(54) CHRYSANTHEMUM PLANT NAMED 'STACY'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/225,015

(22) Filed: Jan. 4, 1999

(51) Int. Cl.[7] ..... A01H 5/00
(52) U.S. Cl. ..... Plt./286
(58) Field of Search ..... Plt./286

*Primary Examiner*—Howard J. Locker
(74) *Attorney, Agent, or Firm*—C. A. Whealy

(57) ABSTRACT

A distinct cultivar of Chrysanthemum plant named 'Stacy', characterized by its uniformly mounded plant habit; relatively early flowering; daisy-type inflorescences that are about 4.8 cm in diameter; attractive white with purple-tipped ray florets and bright yellow disc florets; and numerous inflorescences per plant.

1 Drawing Sheet

BACKGROUND OF THE INVENTION

The present invention relates to a new and distinct cultivar of Chrysanthemum plant, botanically known as *Dendrathema grandiflora* and referred to by the cultivar name Stacy.

The new cultivar is a product of a planned breeding program conducted by the Inventor in Salinas, Calif. The objective of the breeding program is to create new garden-type Chrysanthemum cultivars having inflorescences with desirable inflorescence forms and floret colors and good garden performance.

The new cultivar originated from a cross made by the Inventor in in January, 1993, of two unidentified proprietary seedling selections.

The cultivar Stacy was discovered and selected by the Inventor as a flowering plant within the progeny of the stated cross in a controlled environment in Salinas, Calif., in May, 1994. The selection of this plant was based on its desirable inflorescence form and ray floret color.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Stacy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Stacy'. These characteristics in combination distinguish 'Stacy' as a new and distinct cultivar:

1. Uniformly mounded plant habit.
2. Relatively early flowering.
3. Daisy-type inflorescences that are about 4.8 cm in diameter.
4. Attractive white with purple-tipped ray florets and bright yellow disc florets.
5. Numerous inflorescences per plant.

The new Chrysanthemum is similar to the *Dendranthema grandiflora* cultivar Felicia, disclosed in U.S. Plant Pat. No. 9,809. However in side-by-side comparisons under commercial practice, plants of the new Chyrsanthemum differed from plants of the cultivar Felicia in the following characteristics:

1. Plants of the new Chrysanthemum flower more uniformly than plants of the cultivar Felicia.
2. Plants of the new Chrysanthemum flower about 10 to 14 days later than plants of the cultivar Felicia under natural season conditions.
3. Ray florets of plants of the new Chrysanthemum are white with purple apices whereas ray florets of plants of the cultivar Felicia are solid pink in color.

BRIEF DESCRIPTION OF THE PHOTOGRAPH

The accompanying photograph illustrates the overall appearance of the new cultivar. The photograph comprises a side perspective view of a typical flowering plant of 'Stacy'. This photograph shows the colors as true as it is reasonably possible to obtain in colored reproductions of this type. Floret and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Stacy.

Commercial classification: Daisy-type garden chrysanthemum.

Parentage:

*Female or seed parent.*—Unidentified proprietary seedling selection.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 12 laterals develop.

*Plant height.*—About 26.5 cm.

*Plant spread.*—About 38 cm.

*Foliage description.*—Leaf arrangement: Alternate. Length: About 4.5 cm. Width: About 3.8 cm. Apex: Mucronate. Base: Attenuate. Margin: Palmately lobed, sinuses divergent. Texture: Upper surface very sparsely pubescent; lower surface moderately pubescent. Veins prominent on lower surface. Petiole length: About 1.6 cm. Petiole diameter: About 2 mm. Color: Young foliage upper surface: 147A. Young foliage lower surface: 147B. Mature foliage upper surface: 147A. Mature foliage lower surface: 147B. Venation upper surface: 147B. Venation lower surface: 147B.

Inflorescence description:

*Appearance.*—Daisy-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant, about 15 per lateral stem.

*Flowering response.*—Under natural season conditions, plants flower in late September in the Northern Hemisphere, about 62 days after planting, and flower for at least three weeks depending on weather conditions.

*Inflorescence bud* (*before showing color*).—Height: About 5 mm. Diameter: About 7 mm. Phyllary color: Close to 143A.

*Inflorescence size.*—Diameter: About 4.8 cm. Depth (height): About 8 mm. Diameter of disc: About 1.1 cm.

*Ray florets.*—Shape: Oblong; largest florets occasionally fused, spoon-shaped. Length: About 2.2 cm. Width: About 5.5 mm. Apex: Dentate. Margin: Entire. Texture: Smooth, glabrous. Orientation: Typically horizontal. Number of ray florets per inflorescence: About 68 in several rows. Color: When opening: White, close to 155D. Opened inflorescence: Upper surface: Towards base, white, 155D; apex, purple, 70A to 70B. Lower surface: Towards base, white, 155D; apex, purple, 70B, fading to lighter purple, 75A.

*Disc florets.*—Shape: Tubular, apex dentate. Length: About 5 mm. Width: Apex: About 1.5 mm. Base: About 1 mm. Number of disc florets per inflorescence: About 121. Color Immature: 154A. Mature: Apex: 12A. Mid-section: Very light green. Base: White.

*Peduncle.*—Aspect: Flexible, angled about 45 to 50° to the stem. Length: First peduncle: About 6.5 cm. Fourth peduncle: About 10.6 cm. Diameter: About 2 mm. Texture: Pubescent. Color: 143A.

*Reproductive organs.*—Androecium: Present on disc florets only. Anther color: 12A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Stacy', as illustrated and described.

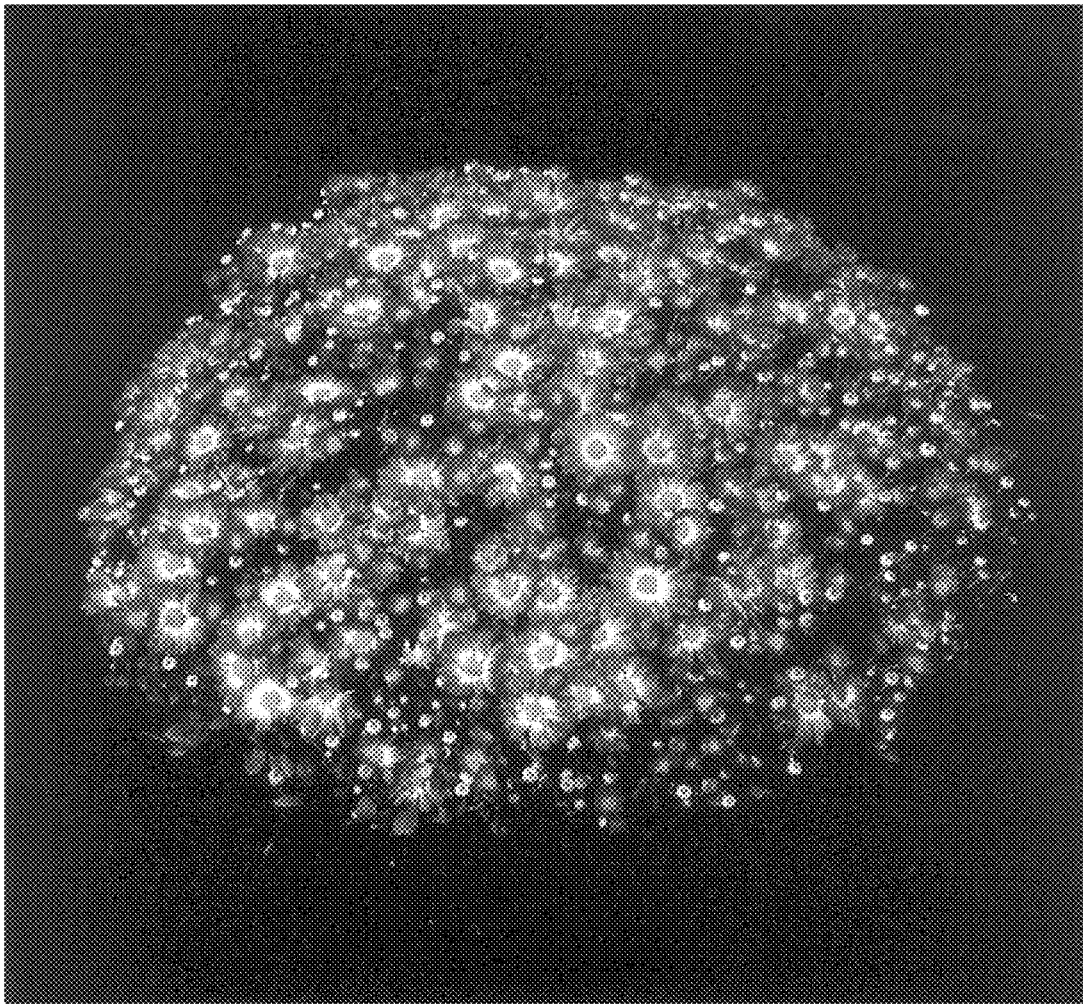

* * * * *